United States Patent
Shen et al.

(10) Patent No.: US 7,700,068 B2
(45) Date of Patent: Apr. 20, 2010

(54) METHOD OF MAKING NIO AND NI NANOSTRUCTURES

(75) Inventors: Wenjie Shen, Liaoning (CN); Yong Li, Liaoning (CN); Mei Cai, Bloomfield Hills, MI (US); Jerry D. Rogers, Rochester Hills, MI (US)

(73) Assignees: GM Global Technology Operations, Inc., Detroit, MI (US); Dalian Institute of Chemical Physica, Chinese Academy of Sciences, Dalian, Liaoning (CN)

( * ) Notice: Subject to any disclaimer, the term of this patent is extended or adjusted under 35 U.S.C. 154(b) by 271 days.

(21) Appl. No.: 11/488,956

(22) Filed: Jul. 19, 2006

(65) Prior Publication Data

US 2008/0019901 A1 Jan. 24, 2008

(51) Int. Cl.
*C01G 53/04* (2006.01)
*C22B 23/02* (2006.01)
(52) U.S. Cl. .................................. 423/594.19; 75/629
(58) Field of Classification Search ............ 423/594.19, 423/629
See application file for complete search history.

(56) References Cited

U.S. PATENT DOCUMENTS

2005/0011310 A1 * 1/2005 Kim et al. ..................... 75/365

OTHER PUBLICATIONS

U.S. Appl. No. 11/069,324, filed Mar. 1, 2005, Cai.
U.S. Appl. No. 11/335,211, filed Jan. 19, 2006, Shen.

* cited by examiner

*Primary Examiner*—Stanley Silverman
*Assistant Examiner*—James Fiorito
(74) *Attorney, Agent, or Firm*—Reising Ethington P.C.

(57) ABSTRACT

The alpha form of nickel (II) hydroxide is formed by dissolving a compound of nickel (II), such as nickel acetate, in a water miscible dihydric alcohol (diol), such as ethylene glycol, propylene glycol and suitable oligomers, and adding a suitable base such as sodium carbonate. The $\alpha$-Ni(OH)$_2$ precipitate is separated from the diol-based mother liquor and dried. This stable $\alpha$-Ni(OH)$_2$ can be calcined at temperatures in the range of about 573K to about 1073K to form nanometer-size particles of NiO having, for example, fibrous shapes. And the small particles of NiO can be reduced with hydrogen to form small, fibrous nickel particles. Both the NiO particles and Ni particles have utility as catalysts and offer utility in applications requiring electronic and/or magnetic properties.

10 Claims, 6 Drawing Sheets

HRTEM images of the nickel hydroxide precipitate.

HRTEM images of the NiO samples by calcination of the as-prepared α-Ni(OH)$_2$. A) 573K; B) 773K; C)973K;D) 1073K HRTEM images of the NiO sample obtained by thermal calcination of the α-Ni(OH)$_2$ at 673K.

HRTEM images of the Ni catalyst by hydrogen reduction of NiO at 773K.

METHOD OF MAKING NIO AND NI NANOSTRUCTURES

TECHNICAL FIELD

This invention pertains to methods of effectively forming α-Ni(OH)$_2$ as very small particles which can be calcined to useful crystalline forms of nickel oxide and further reduced to useful crystalline forms of nickel, all as nanometer-size particles. More specifically, this invention pertains to the use of suitable liquid dihydric alcohols as a solvent and precipitation medium for formation of the precursor, α-Ni(OH)$_2$.

BACKGROUND OF THE INVENTION

It is desired to make nanometer size particles (5 to 30 nanometers in diameter or largest dimension) of nickel and nickel oxide for applications in catalysis, electronics, and magnetics. Several physical and chemical methods such as metal vapor synthesis, thermal decomposition of a nickel aerosol precursor, and sol-gel methods, can be used to synthesize nanocrystalline NiO. The NiO materials prepared by these methods are generally spherical particles with a size of less than ten nanometers when exposed to a temperature less than 400° C. However, the size of these particles increases to greater than about twenty nanometers when they are heated over 700° C. Moreover, there is little control of the morphology of the spherical particles with such methods.

There is a need for a method of producing nanometer size particles of nickel oxide having high temperature stability. There is also a need for producing new crystalline forms (i.e., other than spherical forms) of thermally stable nanometer size particles of nickel oxide.

SUMMARY OF THE INVENTION

Nickel Hydroxide exists in two crystalline forms, an alpha form (α-Ni(OH)$_2$) and a beta form (β-Ni(OH)$_2$). In what follows, α-Ni(OH)$_2$ identifies these hydrotalcite-like compounds without implying any specific stoichiometry. That is to say, the α-form is isostructural with hydrotalcite [Mg$_6$Al$_2$(OH)$_{16}$(CO$_3$)4H$_2$O] and hydrotalcite-like compounds and consists of a stacking of positively charged Ni(OH)$_{2-z}$ layers, with intercalated anions (e.g., carbonate, nitrate, etc.) and water molecules in the interlayer space to restore charge neutrality. The β-form possesses a brucite-like (Mg(OH)$_2$) hexagonal crystal structure and does not contain any intercalated species. α-nickel hydroxide is a metastable phase and is difficult to synthesize because it changes rapidly to the β-form during synthesis or during the storage in a strong alkali, especially in aqueous alkaline solution. In accordance with this invention, a stable form of alpha-nickel hydroxide is prepared as a precursor for calcination to new crystalline forms of nickel oxide. These new crystalline forms of nickel oxide are useful as catalysts. Further, these forms of nickel oxide can be chemically reduced to new crystalline forms of nickel which also have applications as catalysts.

It has been discovered that a suitably stable form of α-Ni(OH)$_2$ can be formed using a precipitation process in which a slightly acidic nickel salt, such as nickel acetate is dissolved in a relatively low molecular weight dihydric alcohol such as ethylene glycol, propylene glycol, and their suitable water-miscible oligomers (The term dihydric alcohol is sometimes shortened to "diol" in this specification). The combination of nickel salt and diol solvent is chosen so that a solution of the salt is obtained at a reasonably moderate temperature such as a temperature below about 400K. Nickel hydroxide is than precipitated form this diol solution by addition of a base, such as sodium carbonate, to the solution. Preferably, the selected diol(s) is miscible with water for convenience in forming and processing the α-Ni(OH)$_2$ precipitate.

In a preferred illustrative example, stable α-Ni(OH)$_2$ with hydrotalcite-like structure was prepared by precipitation of nickel acetate precursor (suitably, nickel (II) acetate tetrahydrate) initially dissolved in ethylene glycol and the solution maintained at 393K. The precipitation of α-Ni(OH)$_2$ was accomplished by adding an aqueous solution of sodium carbonate to the glycol solution of nickel acetate as the solution was stirred. Despite the use of water in the sodium carbonate addition a very finely divided precipitate of α-Ni(OH)$_2$ was obtained due to the mediation of the glycol medium. After the α-Ni(OH)$_2$ was separated from the mother liquor and dried it was found that it could be used to consistently and readily form new crystalline forms of nickel oxide and nickel which could be produced as useful nanometer size particles. The particles were typically in the form of fibers with fiber diameters in the low nanometer-size range, typically less than about twenty nanometers or so.

Thermal calcination of the α-nickel hydroxide at temperatures over the range of 573 to 1073 K resulted in the formation of novel nickel oxides with crystalline fibrous shapes and crystallite sizes (by XRD) of 3.0 to 8.1 nm. At the micrometer scale the material is seen as a mass of tangled fibers. At the nanometer scale more ordered fibers or flakes are seen.

Further, reduction of these NiO samples with hydrogen at 773 K led to the formation of fibrous metallic Ni catalysts with fiber diameters of about 11 nm. Most promisingly, these fibrous Ni materials showed much higher catalytic activities not only for the hydrogenation reactions of unsaturated organic compounds, but also for the hydrogen production from methane decomposition with the carbon yield as high as 492 g C/g Ni.

Other objects and advantages of the invention will become apparent from descriptions of preferred embodiments.

DESCRIPTION OF PREFERRED EMBODIMENTS

Introduction

Figure 1:
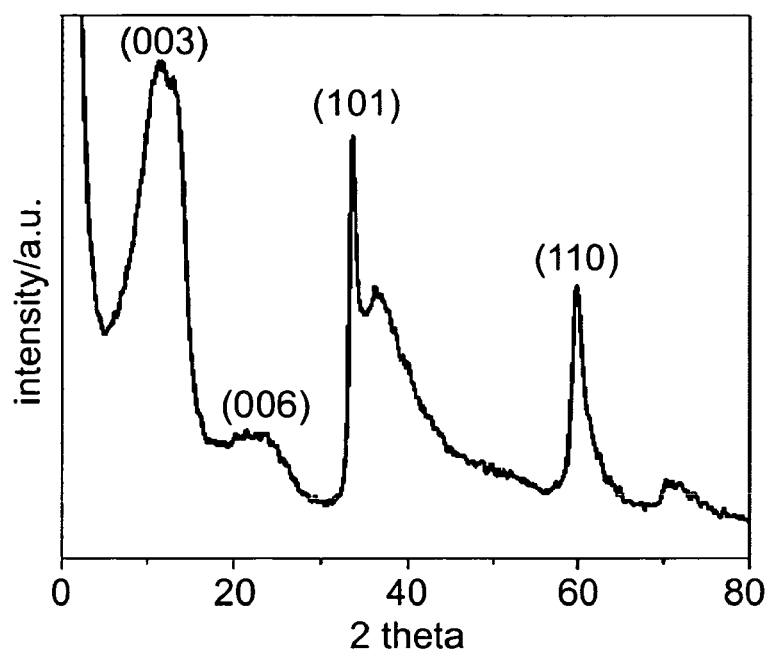
FIG. 1 is an x-ray diffraction (XRD) pattern of an α-nickel hydroxide precipitated from an ethylene glycol medium in accordance with this invention.

Nanosized nickel materials in new and controllable morphologies show interesting chemical and physical properties for the potential applications in the fields of catalysis, electronics and magnetism.

Nickel hydroxide prepared in a liquid medium is an important intermediate for the synthesis of nickel oxide and metallic nickel. This solid precursor is usually present as β-Ni(OH)$_2$ because of its thermodynamic stability in this form, especially in alkaline media. However, thermal calcination of β-Ni(OH)$_2$ results in the formation of spherical NiO particles, and the particle size is critically dependent on the calcination temperature. Lower temperature calcination (573 K) yields particle sizes of NiO less than 10 nm, while much larger particles, more than 20 nm, are produced when the calcination is performed at relatively higher temperatures (>773 K). Recently, β-Ni(OH)$_2$ in the forms of nanometer-size rods, sheets, ribbons, tubes, pancakes and hollow spheres have been successfully prepared as solids in a liquid phase such as water. Accordingly, nickel oxides with various structural features have been obtained by workers by thermal decomposition of those β-Ni(OH)$_2$ precursors. For instance, NiO nanorings were produced by calcination of β-Ni(OH)$_2$ nanorods at 773K, and NiO nanosheets were prepared by thermal decomposition of β-Ni(OH)$_2$ nanosheets at 673K.

However, it has proven difficult to prepare stable α-Ni(OH)$_2$ with hydrotalcite-like structures in a liquid medium, such as water, since it rapidly turns into β-Ni(OH)$_2$. Precipitation of nickel salts with liquid ammonium hydroxide, cathodic reduction of nickel nitrate, homogeneous urea hydrolysis of nickel nitrate, and sonochemical synthesis have been proposed to be effective for getting stable α-Ni(OH)$_2$. Obviously, there is still a lack of a mild and fast chemical route to synthesize stable α-nickel hydroxide in a liquid medium. Because of this, decomposition of α-Ni(OH)$_2$ for producing nanosized NiO materials with controlled morphologies has not been reported.

In accordance with a preferred embodiment of this invention, stable α-Ni(OH)$_2$ is prepared by precipitation of nickel acetate from an ethylene glycol medium by the addition of a base, for example, sodium carbonate. The sodium carbonate may be added as an aqueous solution to the diol solution of the nickel acetate. The precipitated α-Ni(OH)$_2$ is ultimately used as a precursor to produce fibrous NiO and Ni nanometer-size materials. The use of the ethylene glycol medium (rather than water, for example) for the formation of α-Ni(OH)$_2$ provides an easy and low cost route for preparing size-controlled and morphology-controlled nanometer size nickel oxide and nickel particles. Other suitable water-miscible dihydric alcohols or mixtures of such alcohols may be used. Moreover, the resulting Ni nanomaterials also showed very high catalytic activities for hydrogenation of unsaturated organic compounds and methane cracking reaction.

EXPERIMENTAL

Preparation of Materials

Alpha-nickel hydroxide was prepared at 393 K by precipitation of nickel acetate dissolved in ethylene glycol with the addition of sodium carbonate aqueous solution. A solution containing 0.05 mol of nickel acetate (Ni(OAc)$_2$ 4H$_2$O) and 150 mL of ethylene glycol (EG) was gradually heated to 393 K with stirring and maintained at this temperature for 30 min. Then, 500 mL of 0.2 M Na$_2$CO$_3$ aqueous solution was slowly added into the Ni acetate-EG mixture reaching a final pH value of about 10. A precipitate was formed and it was further aged in the ethylene glycol/water mother liquid for one hour. The precipitate was separated from the mother liquor by filtration and thoroughly washed with distilled water. The obtained solid was dried at 373 K overnight. As described below, this solid material was confirmed to be α-Ni(OH)$_2$.

A series of nickel oxides were then obtained by thermal calcination of the nickel hydroxide in air at temperatures over the range of 573-1073 K for four hours. Chemical reduction of the nickel oxides with hydrogen at 773 K led to the formation of metallic nickel.

Characterization of the Formed Products.

Nitrogen adsorption-desorption isotherms were performed using a Nova 4200e (Quantachrome) system operated at 77 K. Prior to measurement, the sample was degassed by vacuum at 573 K for 5 h. The BET surface area was calculated from a multipoint Braunauer-Emmett-Teller analysis of the nitrogen adsorption isotherms.

X-ray powder diffraction (XRD) patterns were recorded on a D/MAX 2500 X-ray diffractometer (Rigaku), using Cu Kα radiation operated at 40 kV and 100 mA. In situ XRD measurements of the reduction of NiO samples with hydrogen were performed in a high temperature chamber installed in the diffractometer. The NiO was pressed into flake and mounted in the chamber. After heating to 773 K in the flow of Ar, pure hydrogen was then introduced into the chamber and kept at 773 K for 1 h, and then the XRD patterns were recorded. The mean crystallite sizes of nickel and NiO were calculated from the Scherrer equation, where the particle shape factor was taken as 0.9.

HRTEM images were taken on Philips Tecnai G$^2$20 operated at 200 kV. Specimens were prepared by ultrasonically suspending the sample in ethanol. A drop of the suspension was then applied onto clean copper grids and dried in air. For HRTEM observation of the Ni catalyst, the NiO sample was first reduced with hydrogen in a continuous flow fixed-bed reactor at 773 K for 1 h. After cooling down to room temperature under Ar flow, anhydrous ethanol was then introduced through a syringe pump with Ar as carrier gas until the reduced sample was all immersed. Then it was quickly transferred and stored in the bottle of ethanol.

Thermal gravity and Differential Thermal Analysis (TG-DTA) of the nickel hydroxide was measured on the Pyris Diamond of Perkin Elmer from room temperature to 773 K under the flowing of air. FT-IR spectra were obtained by transmission on a Bruker Vector 22 spectrometer on pressed KBr pellets in the range of 400-4000 cm$^{-1}$ with 4 cm$^{-1}$ resolution. UV-visible diffuse reflectance spectra were recorded on a JASCO V-550 spectrometer in the range of 190-900 nm.

Temperature-programmed reduction (TPR) was performed in a conventional setup equipped with TCD detector.

In typical runs, 50 mg NiO samples were used and heated to 673 K (10 K/min) under $N_2$ flow (40 ml/min) and kept at this temperature for one-half hour to remove the adsorbed carbonates and hydrates. After cooling down to room temperature and introducing the reduction agent of 20 vol % $H_2/N_2$ (40 ml/min), the temperature was then programmed to rise at a ramp rate of 10 K/min from 303 K to 1073 K.

Catalytic Testing.

Hydrogenation reaction of unsaturated organic compounds was carried out with a conventional gas-flow reactor system. 100 mg NiO samples were packed in a tubular reactor (diameter of 8 mm and length of 300 mm) made from quartz. Then, NiO particles were reduced to metallic Ni particles by hydrogen flow at 773 K for one hour and flushed with Ar. The unsaturated organic substrate was injected by a syringe pump (Sage instruments, model 355) and helium carrier gas was introduced through a mass-flow controller. The effluents from the reactor were analyzed by on-line gas chromatography.

Methane decomposition reaction was carried out in a continuous flow fixed-bed quartz reactor at 773 K under atmospheric pressure. 40 mg NiO samples were loaded and pre-reduced into metallic Ni catalyst with pure hydrogen (20 ml/min) at 773K for one hour. The Ni catalyst was flushed with argon for one-half hour. Methane (99.995% purity, 60 ml/min) was then introduced through a mass flow controller. The effluents from the reactor were analyzed by on line gas chromatography. Hydrogen was detected as the only product, indicating that the methane cracking occurred as $CH_4 \rightarrow C + 2H_2$. Accordingly, the methane conversion was calculated from the amounts of the carbon required to produce a quantity of hydrogen.

Results and Discussion

Structural Characterizations of Nickel Hydroxide.

FIG. 1 shows the XRD pattern of the as-prepared nickel hydroxide precipitate. Clearly, this precipitate exhibited characteristic diffractions of $\alpha$-Ni(OH)$_2$ (JCPDS #38-0715), which is isostructural with hydrotalcite-like compounds. No diffraction peaks due to $\beta$-Ni(OH)$_2$ (JCPDS #14-0117) could be observed. The typical peaks at about d=7.56, 3.78, 2.66, and 1.54 A can be assigned to the (003), (006), (101) and (110) planes, respectively, indicating the formation of $\alpha$-Ni(OH)$_2$.

Figure 2:
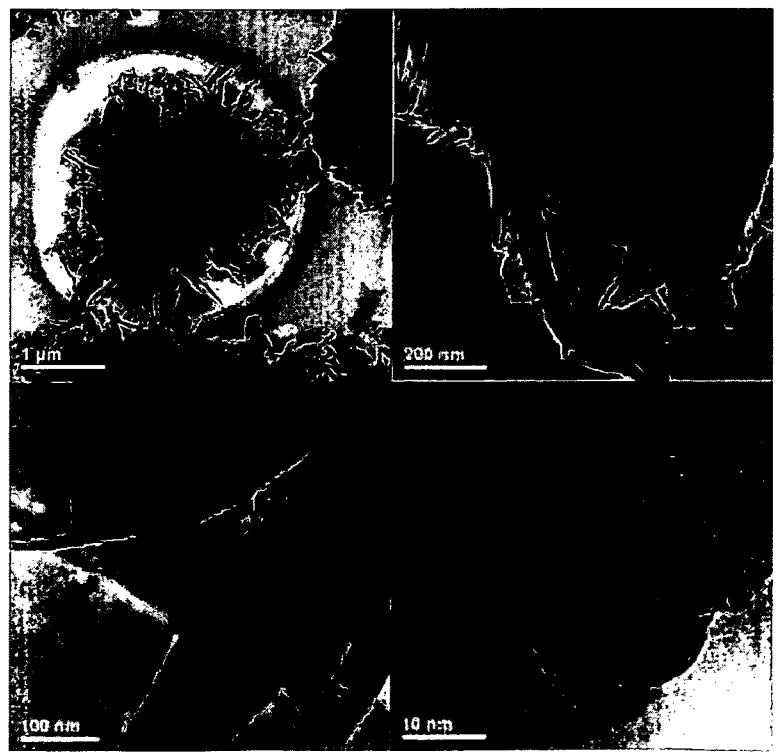
FIG. 2 is a grouping of four high resolution transmission electron microscope (HRTEM) images at different magnification of the α-nickel hydroxide precipitate.

FIG. 2 shows four high resolution transmission electron microscope images of an $\alpha$-Ni(OH)$_2$ precipitate. The particles are in the form of fibers with diameters generally less than about 10 nanometers and greater lengths Nickel Oxides Obtained by Thermal Calcination of $\alpha$-Ni(OH)$_2$.

Figure 3:
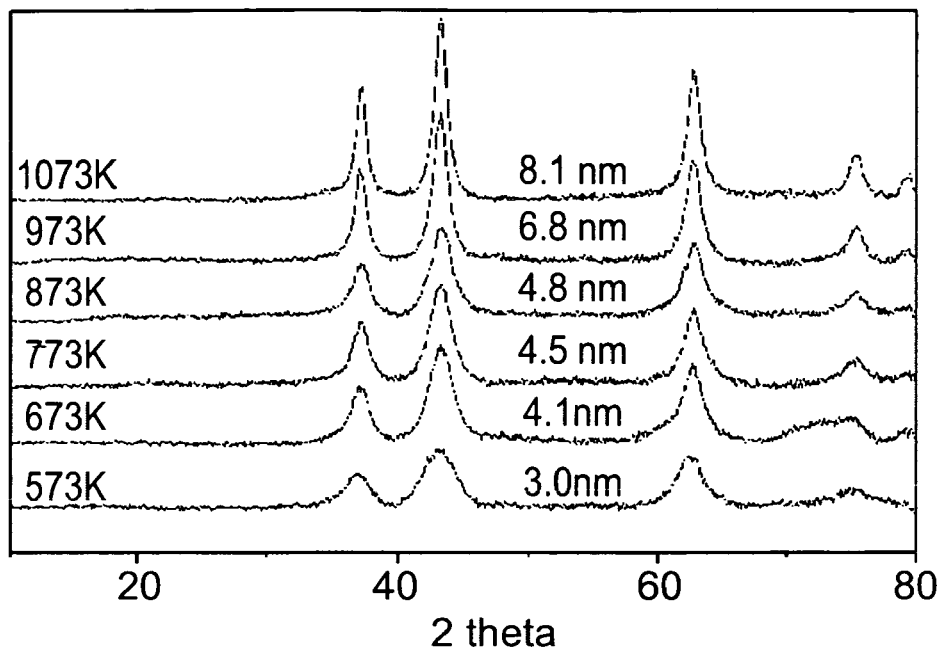
FIG. 3 is a group of XRD patterns of NiO samples obtained by calcining α-nickel hydroxide at six temperatures; 573K, 673K, 773K, 873K, 973K, and 1073K, respectively. The six diffraction patterns (intensity, a.u. vs. two-theta angle) located successively above each other with increasing calcination temperature each confirmed the formation of nanometer-size diameter fibrous particles of face-centered cubic nickel oxide.

Samples of the $\alpha$-Ni(OH)$_2$ precipitate were then calcined in the temperature range of 573-1073 K. Samples were calcined at 573K, 673K, 773K, 873K, 973K, and 1073K. As shown in FIG. 3, the obtained NiO samples exhibited typical face-centered cubic structure of nickel oxide (JCPDS #4-835), regardless of calcination temperature. The half-widths of the diffraction peaks of nickel oxides were gradually becoming narrower with increasing calcination temperature, indicating the growth of NiO crystallites. With increasing calcination temperature from 573 K to 1073 K, the crystallite size of NiO only increased from 3.0 nm to 8.1 nm and the surface area slightly decreased from 147 $m^2g^{-1}$ to 79 $m^2g^{-1}$.

Figure 4:
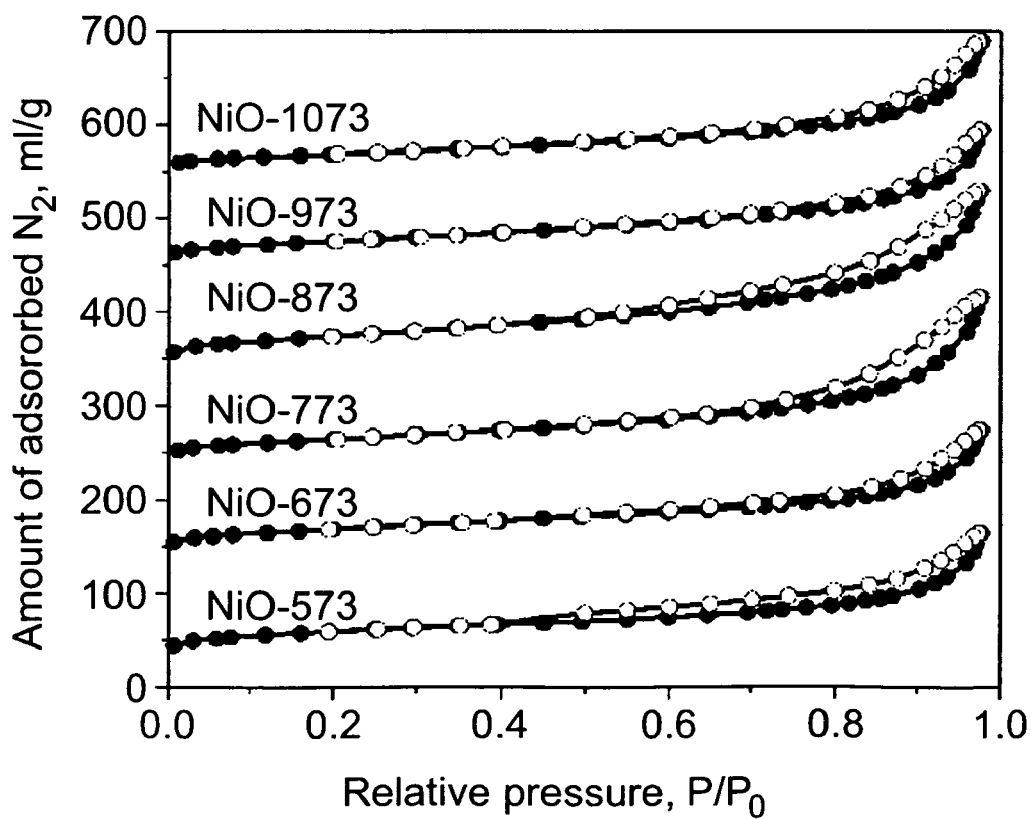
FIG. 4 presents successive nitrogen adsorption-desorption isotherms of the six nickel oxide samples produced by calcining α-nickel hydroxide at 573K, 673K, 773K, 873K, 973K and 1073K, respectively.

FIG. 4 illustrates the nitrogen adsorption-desorption isothermals of the nickel oxides. The isotherms showed H4-type hysteresis loop in the IUPAC classifications, indicating the open slit-shaped capillaries with very wide bodies and narrow short necks. The weak adsorption of $N_2$ molecules at low p/po region and the distinct hysteresis at p/po>0.5 implied that most of the porosity originated from the mesopores in the stacked structure of NiO crystallites, which is similar to the layered Ti—Zn oxides. It is worthy to note that the NiO nanomaterials still showed marked hysteresis with mesoporosity even after calcination at 1073 K, indicating the high stability of the pore-structure.

Figure 5:
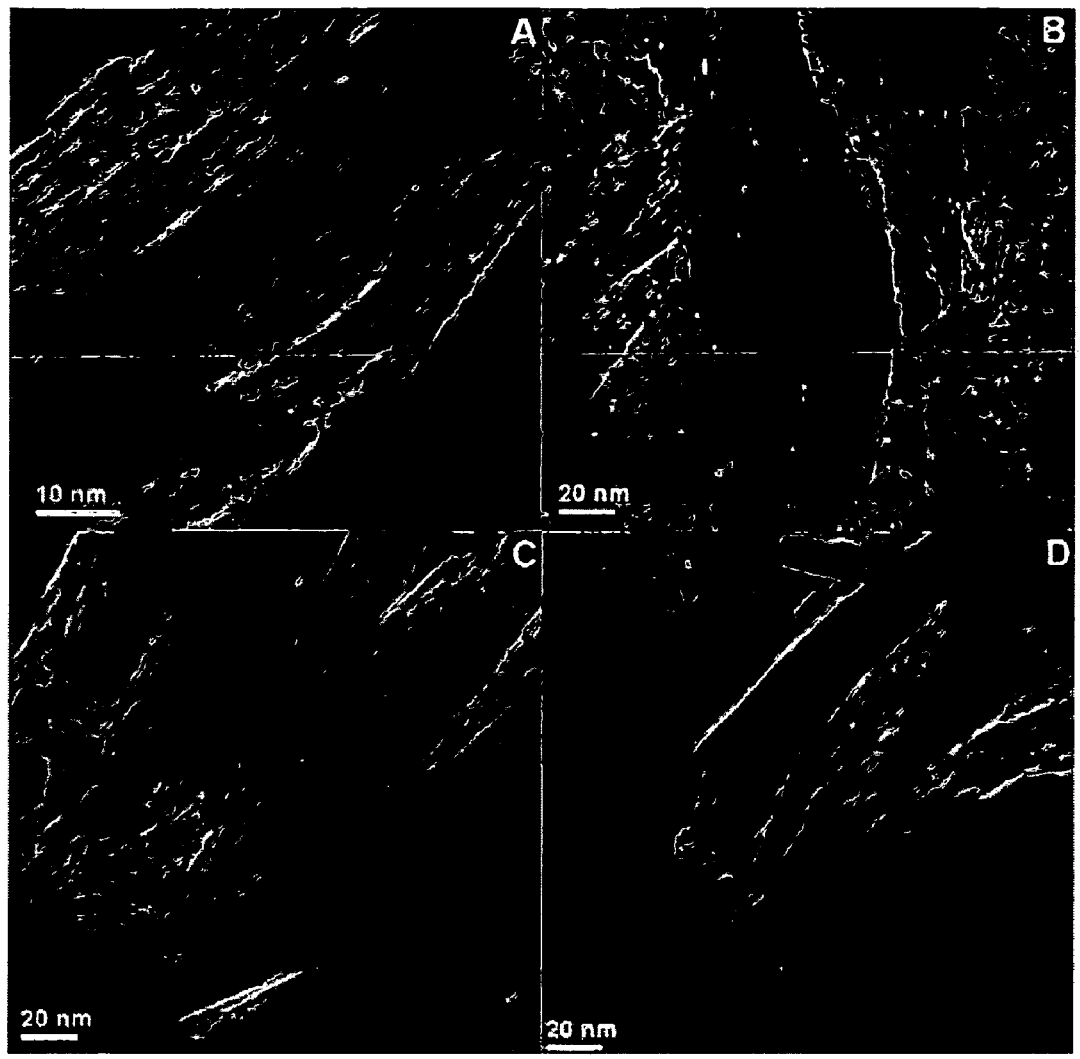
FIG. 5 is a cluster of four HRTEM images of the NiO samples produced by calcination of α-nickel hydroxide at 573K, 773K, 973K, and 1073K, respectively.

FIG. 5 presents four HRTEM images of the NiO samples produced by calcining the subject samples of $\alpha$-Ni(OH)$_2$ by calcining at 573K (image A), 773K (image B), 973K (image C) and 1073K (image D). It can be seen that the interlayer structure of $\alpha$-Ni(OH)$_2$ still remained in the nickel oxides even after calcination at 1073 K, and the bundles turned to be shorter with increasing calcination temperature.

Figure 6:
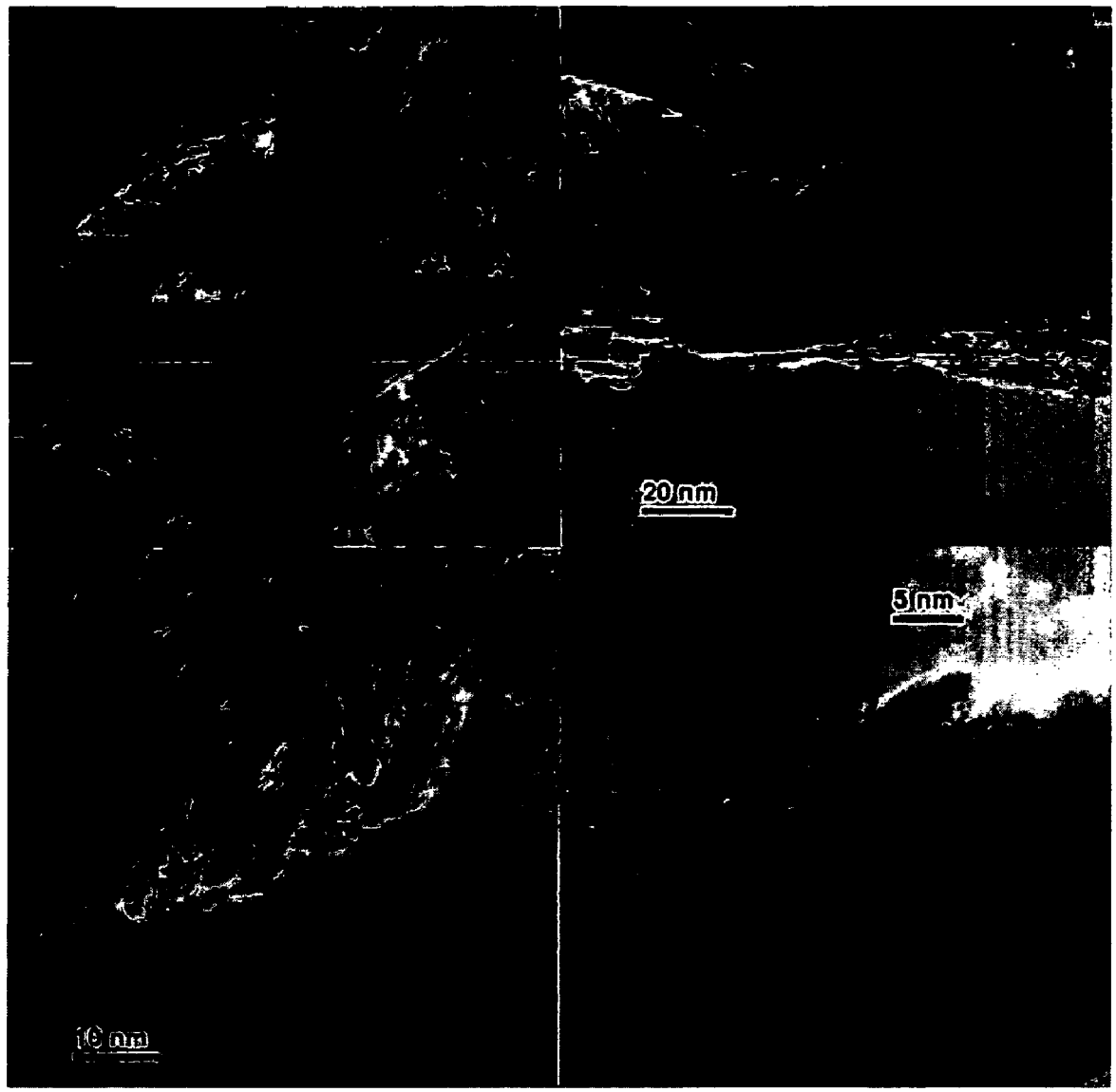
FIG. 6 is a cluster of four HRTEM images at different levels of magnification of the NiO sample obtained by calcination of α-nickel hydroxide at 673K.

FIG. 6 presents four HRTEM images of NiO samples produced by calcining the $\alpha$-Ni(OH)$_2$ at 673K. The images are at progressively larger magnification starting in the upper left corner of FIG. 6. These images further demonstrate the characteristic fibrous shapes of the NiO materials obtained by thermal calcination of nickel hydroxide at 673 K. Clearly, the length of the fibrous NiO approached to several hundreds of nanometers and the fiber diameter was about 4 nm.

These observations are quite promising for NiO materials, since the previously reported nickel oxides often showed spherical shapes and relatively weak thermal stability. A careful survey of the previous studies on NiO materials may find that the obtained spherical NiO particles were small size (<10 nm) with a high surface area only after low temperature calcinations ($\leq$673 K), while very large nanoparticles (>20 nm) were produced once the calcination was performed at relatively higher temperatures (~973K). Up to date, there is little work on the preparation of NiO nanostructures with high temperature stability and non-spherical morphology. Thus, the present study achieved not only the rather small crystalline size of NiO, but also the most interesting fibrous shapes from the nickel hydroxide precipitate to the nickel oxides.

Metallic Ni Obtained by Hydrogen Reduction of NiO.

Since metallic nickel is the active component in the heterogeneous catalysis, the NiO sample obtained by calcination of the $\alpha$-Ni(OH)$_2$ was further reduced with hydrogen to get metallic Ni catalyst. For comparison, the NiO samples obtained by calcining the nickel hydroxide at 673 K and 1073 K were selected to investigate the evolution of NiO during hydrogen reduction by in situ XRD measurements. The diffraction patterns are not shown here but the nickel oxides exhibited similar reduction behavior with increasing reduction temperature, although their initial crystalline sizes of NiO were 4.1 nm and 8.1 nm, respectively. The metallic nickel phase (JCPDS #4850) appeared after reduction at 573 K and the diffraction peaks of NiO almost vanished at 673 K, suggesting that NiO was completely converted to metallic nickel. With further increase of the reduction temperature, the diffraction peaks of metallic Ni were gradually becoming extensive and sharper, indicating the enlarging of metallic Ni crystallites. After reduction with hydrogen at 773 K, the resulting metallic Ni crystalline sizes were 9.0 nm and 10.2 nm, respectively, for the two samples. The crystallite sizes of metallic nickel further increased to 24.0 nm and 24.8 nm after reduction at 973 K.

Figure 7:
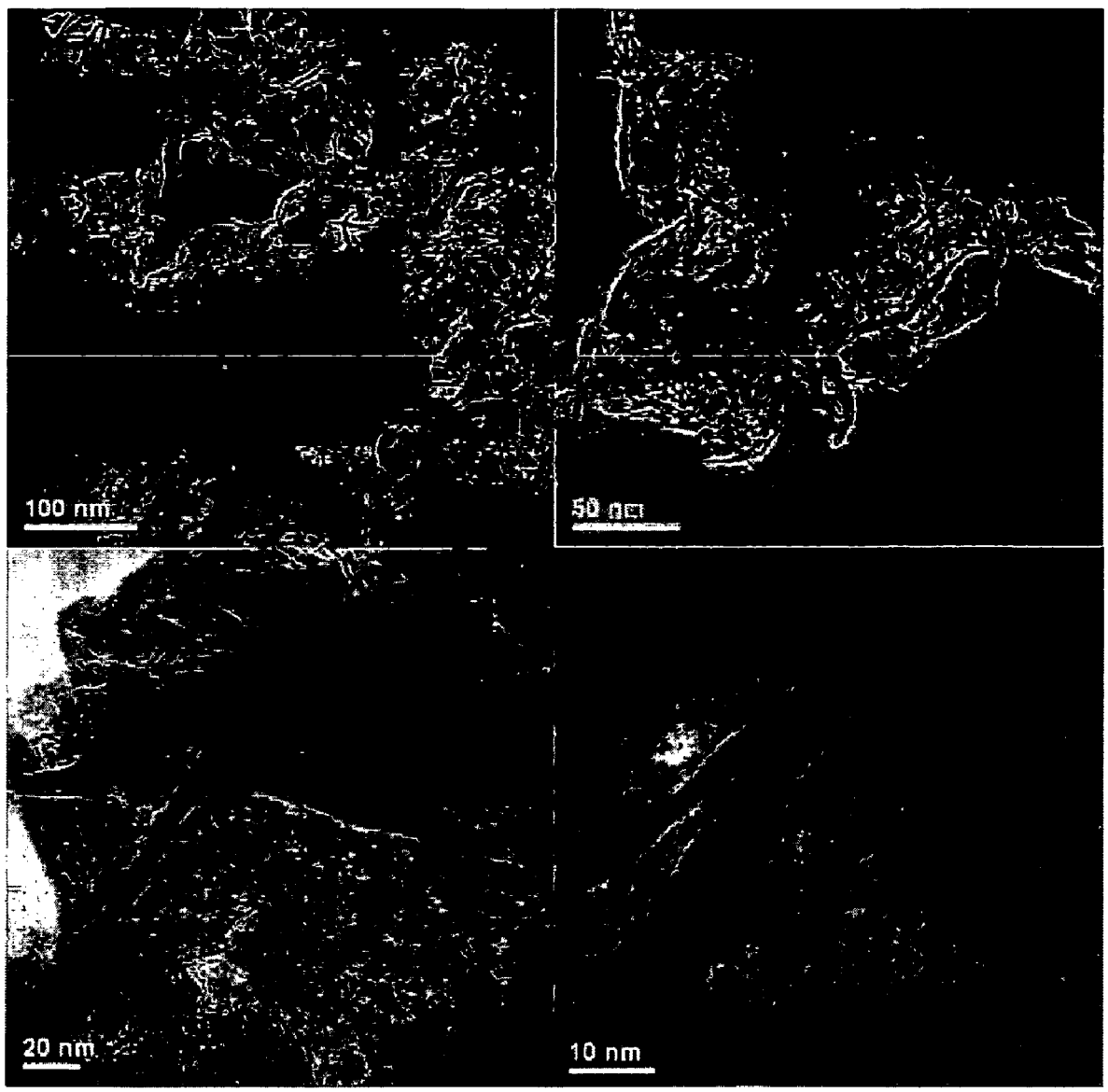
FIG. 7 is a grouping of four HRTEM images of Ni particles produced by hydrogen reduction of NiO particles at 773K in accordance with this invention.

More importantly, the fibrous-like morphology still remained in the obtained metallic Ni catalysts, as shown in the four HRTEM images presented in FIG. 7. These images show the fibers of nickel at progressively larger magnification starting with the upper left image of the grouping. Only whisker-like morphology of metallic nickel supported by $SiO_2$ was previously synthesized by carefully control of the reduction step, and this novel structure could only be achieved with much lower nickel loading (≦2%) and the surface area of silica must be less than 15 m²/g.

Hydrogen-temperature programmed reduction ($H_2$-TPR) profiles were obtained of the fibrous NiO and the reference NiO sample. These profiles clearly showed a strong and sharp hydrogen consumption peak at around 600 K for the reference NiO, representing the characteristic reduction of stoichiometric nickel oxide. However, the fibrous NiO exhibited a relatively broadened hydrogen consumption peak at higher temperature (675 K). It was stated that the reduction temperature of NiO increased with increasing the particle size of NiO in the range of 6~17 nm, but there are few reports on the effect of morphology on the reduction behavior of NiO. For the current fibrous NiO, the calculated crystalline size of NiO was only 4.1 nm, and it should be practically and easily reduced into metallic Ni at lower temperatures. But its reduction was completed at higher temperature than a reference NiO sample (crystalline size of 8.4 nm). Therefore, it is reasonable to speculate that the interlayered structure of the fibrous NiO sample hindered the reduction of NiO. As a matter of fact, $H_2$-TPD studies of a Ni/SiO$_2$ catalyst have already revealed that the morphology can indeed influence the desorption features of metallic nickel, and the nickel in whisker shapes are more reactive towards hydrogen than spherical nickel. Therefore, the interlayered fibrous structure of the current NiO may greatly influence its reduction features, resulting in significant difference in the TPR profiles compared with normal spherical NiO particles. Although there were many reports on the preparation of nanosized metallic nickel materials with controlled morphologies using different methods, it does not appear that the NiO and Ni with the same fibrous-like shapes have been reported so far.

Catalytic Performance of Fibrous Ni Catalysts.

Ni-based catalysts mainly in the form of metallic nickel have been widely used in heterogeneous catalytic reactions, like hydrocarbon conversion, hydrosulfurization of fuels and hydrogenation of unsaturated organic compounds. Recently, catalytic cracking of methane over supported nickel catalyst has received much attention as a potentially economical route to produce CO-free hydrogen for fuel cell applications. Such nickel catalysts are produced by in situ hydrogen reduction of NiO immediately prior to methane cracking. Ni catalysts were extensively designed and examined for methane decomposition due to their relatively higher activities than other transition metals. The most important factor that influences the carbon yield during methane decomposition is the particle size of the metallic nickel, and thus great efforts have been paid to disperse and stabilize the nickel particles by selecting appropriate support. In principle, the use of a catalyst containing only metallic Ni phase without the presence of any support would give sufficient carbon storage capacity on a per-gram basis of the catalyst and also provide an additional advantage to the easy removal of catalyst components for the carbon nanofibers. The NiO samples obtained by calcining the nickel hydroxide precursor at 573-1073 K were reduced with hydrogen at 773 K, and the obtained metallic Ni catalysts were investigated for the reaction of methane decomposition.

Table 1 summarizes the accumulated carbon and hydrogen yields during methane cracking over these novel Ni catalysts. The table refers to the NiO precursors because the nickel catalyst was produced by in situ reduction of a NiO sample immediately prior to the methane decomposition test.

TABLE 1

Effect of calcination temperature on the physical properties and the catalytic activities of unsupported NiO catalysts for methane decomposition.

| Catalysts | $D^{XRD}$ (nm)[a] | B.E.T (m²/g) | $H_2$ yield (mol $H_2$/mol Ni) | carbon yield (g C/g Ni) |
|---|---|---|---|---|
| NiO-573K | 3.0 | 147 | 3463 | 354 |
| NiO-673K | 4.1 | 123 | 3894(4814[b]) | 398(492[b]) |
| NiO-773K | 4.5 | 117 | 3854 | 394 |
| NiO-973K | 6.8 | 97 | 3786 | 387 |
| NiO-1073K | 8.1 | 79 | 3727 | 381 |

[a]NiO crystallite sizes determined by XRD
[b]Data obtained with pure methane flow rate of 30 ml/min Interestingly, there were no significant changes observed in the methane conversions, although their initial crystalline sizes of NiO were dependent on the calcination temperature. When the crystalline size of NiO increased from 3.0 nm to 8.1 nm, the carbon yield only altered in the range of 354-394 g C/g Ni, and the corresponding hydrogen yield slightly varied between 3463 mol Hz/mol. Ni and 3854 mol $H_2$/mol. Ni. When the methane flow rate decreased to 30 ml/min, the carbon yield over the novel Ni catalyst could further increase to 492 g C/g Ni with the hydrogen yield of 4814 mol $H_2$/mol. Ni. This result is very similar to the highest carbon yield of 491 g C/g Ni, which was obtained over the most effective 40% Ni/SiO$_z$ catalyst in the literature.

Figure 8:
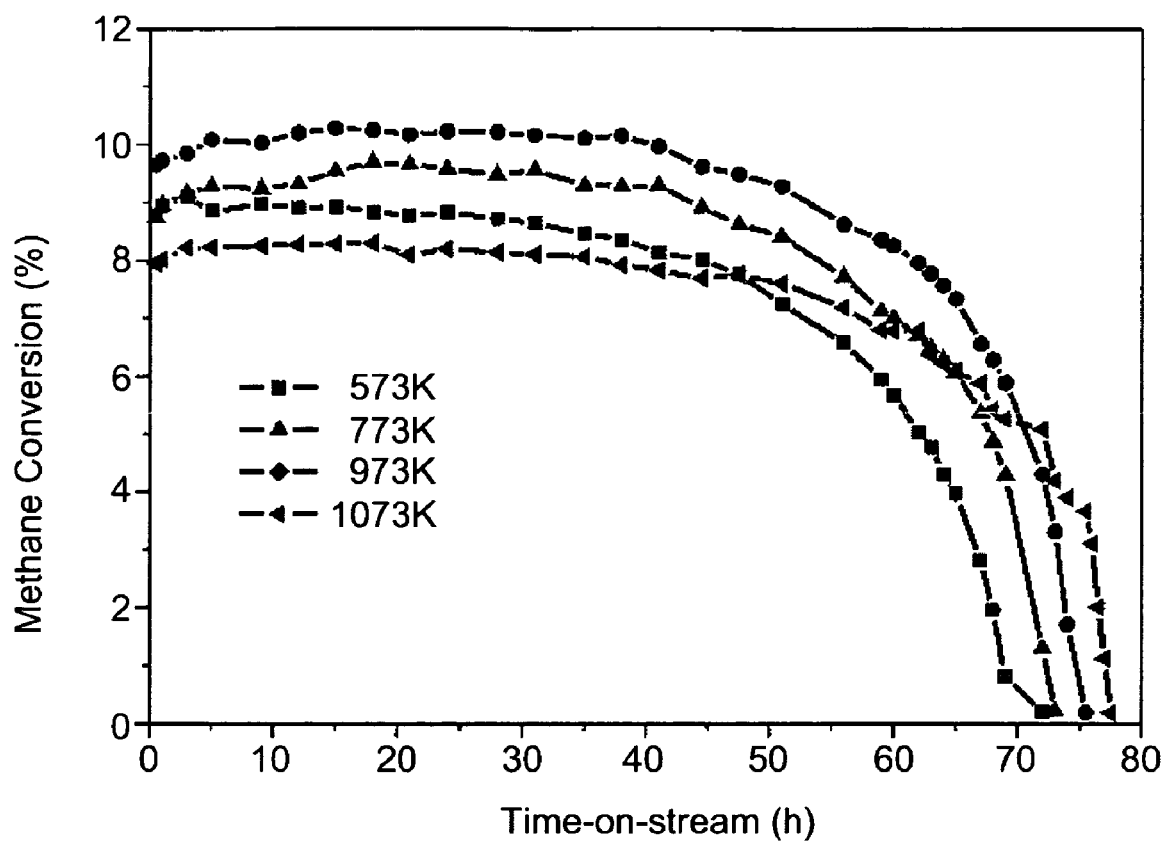
FIG. 8 graph of percent of methane conversion at different reactor temperatures vs. time-on-stream in hours over NiO catalysts prepared by calcination of α-nickel hydroxide at 773K in accordance with this invention.

FIG. 8 graphically presents percent methane conversion versus time on stream for the nickel catalysts made from NiO precursors that were made by calcining alpha-nickel hydroxide precursors at 573K, 773K, 973K, and 1073K, respectively.

The typical NiO sample obtained by calcination of nickel hydroxide at 673 K was further reduced into metallic Ni with hydrogen at 773 K. The obtained Ni catalyst was then employed for gas-phase hydrogenation of unsaturated organic compounds in a continuous flow fixed-bed reactor at atmospheric pressure.

TABLE 2

Hydrogenation test of different substrate using Ni as catalyst[a]

| Substrate | Hydrogenation Temp (K) | Selectivity (%) | Conversion (%) |
|---|---|---|---|
| benzene | 373 | Cyclohexane~100 | >99.5 |
| acetone | 373 | Isopropanol~100 | >95 |
| nitrobenzene[b] | 373 | Aniline~90 | >99 |
| phenol[c] | 473 | cyclohexanol~88 cyclohexanone~12 | >99 |

[a]$H_2$: 20 ml/min; liquid feed rate: 0.00667 ml/min, 100 mg catalyst
[b]$C_6H_5NO_2$:$C_6H_{12}$ = 1:1(vol)
[c]$C_6H_5OH$:$C_6H_{12}$ = 1:4(wt).

Figure 9:
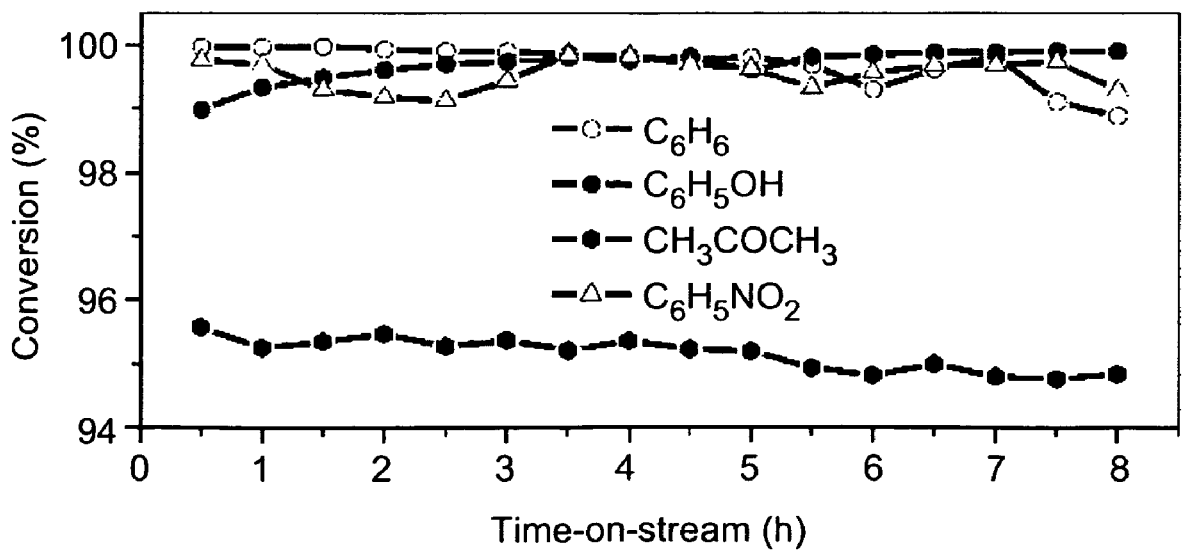
FIG. 9 is a graph of % conversion of hydrogenation of unsaturated substrates over a fibrous nickel catalyst produced in accordance with this invention.

As shown in Table 2, the Ni catalyst showed higher activity and selectivity not only in the hydrogenation of benzene and acetone, which are two model substrates of hydrogenation, but also in the hydrogenation of nitrobenzene to aniline and phenol to cyclohexanol with rather stable catalytic durability. FIG. 9 presents the percent conversion data versus tine on stream in hours for these hydrogenation reactions catalyzed by the fibrous nickel material.

Currently, the industrial hydrogenations of these unsaturated organic compounds are performed in batched-scale autoclaves using Raney Ni catalyst under sever conditions. For example, hydrogenation of benzene to cyclohexane is conducted at 493 K and 4.0 MPa of $H_2$ according to the IFP process. While this novel fibrous Ni catalyst can give a 100% conversion of benzene at 373 K under atmospheric pressure in continuous flow operation. In the case of phenol hydrogenation to cyclohexanol, it is industrially performed at 373 K and 13~15 MPa of $H_2$ by using Raney Ni catalyst, while the present continuous flow operation using the fibrous Ni catalyst could give 100% conversion of phenol and 88% selectivity of cyclohexanol at 473 K.

Obviously, this novel Ni catalyst generated from the NiO precursor showed much higher catalytic activity in hydrogenation of organic substrates under much milder conditions. Another important superiority of this fibrous Ni catalyst over the Raney Ni catalyst lies in the environmental begin and cost-efficiency of its preparation. Raney Ni catalyst, also known as sponge, skeletal, or activated metals, are traditionally produced by the removal of aluminum from a Ni/Al alloy with a strong alkaline solution. Clearly, this kind of preparation process does not meet the up-to-date requirements of resources saving by considering the leaching of aluminum from binary alloys, the heavy pollution of alumina-rich alkaline wastes, and the operating safety due to inflammable. Therefore, such a solution phase approach through nickel hydroxide and nickel oxide precursors may provide a more promising route for preparing size and morphology-controlled Ni catalyst than the current method of Raney Ni in terms of cost and environmental impact.

CONCLUSION

α-Ni(OH)$_2$ with hydrotalcite-like structures may be successfully prepared in liquid phase with the mediation of ethylene glycol, a propylene glycol, or other suitable water-miscible dihydric alcohol. Thermal calcination of this nickel hydroxide precursor resulted in the formation of novel NiO nanomaterials with interlayered structures. Such a solution phase approach provided a more promising route for preparing size and morphology-controlled NiO nanomaterials. Further reduction of the NiO with hydrogen led to the formation of fibrous metallic nickel catalysts with, which showed extremely high catalytic activities towards hydrogenations of organic substrates and methane cracking reaction.

While the invention has been illustrated in terms of some preferred illustrative embodiments, the scope of the invention is not limited to the illustrations.

The invention claimed is:

1. A method of forming α-Ni(OH)$_2$ comprising:
   dissolving a salt of nickel (II) in a liquid dihydric alcohol that is miscible with water, the liquid dihydric alcohol initially containing no water other than water of crystallization present in the selected nickel (II) salt, the solution containing Ni (II) ions;
   precipitating Ni (II) ions as nickel hydroxide from the alcohol solution by the addition of a base to the solution; and
   separating the nickel hydroxide precipitate from the mother liquor to recover α-Ni(OH)$_2$ in the form of fibers with nanometer size diameters.

2. A method of forming α-Ni(OH)$_2$ as recited in claim 1 in which the salt of nickel (II) is nickel acetate or nickel acetate tetra-hydrate.

3. A method of forming α-Ni(OH)$_2$ as recited in claim 1 in which the liquid dihydric alcohol solvent is an alcohol selected from the group consisting of ethylene glycol and propylene glycol.

4. A method of forming α-Ni(OH)$_2$ as recited in claim 1 in which the base is an aqueous solution of sodium carbonate.

5. A method of forming nanometer-size particles, the method comprising:
   dissolving a salt of nickel (II) in a liquid dihydric alcohol that is miscible with water, the liquid dihydric alcohol initially containing no water other than water of crystallization from the nickel (II) salt, the solution containing Ni (II) ions;
   precipitating Ni (II) ions as nickel hydroxide from the alcohol solution by the addition of a base to the solution;
   separating the nickel hydroxide precipitate from the mother liquor to recover α-Ni(OH)$_2$; and
   calcining the α-Ni(OH)$_2$ to form fiber shaped particles of nickel oxide.

6. A method of forming nanometer-size particles as recited in claim 5, the method further comprising:
   reducing the particles of nickel oxide with hydrogen to form particles of nickel.

7. A method of forming nanometer size particles as recited in claim 5 in which the liquid dihydric alcohol is an alcohol selected from the group consisting of ethylene glycol and propylene glycol; and
   calcining the α-Ni(OH)$_2$ in air to form fiber shaped nickel oxide particles.

8. A method of forming nanometer-size particles as recited in claim 7, the method further comprising:
   reducing the particles of nickel oxide with hydrogen to form nanometer-size particles of nickel that are fiber shaped.

9. A method of forming nanometer-size particles, the method comprising:
   dissolving nickel (II) acetate in ethylene glycol, the ethylene glycol containing no water other than water of crystallization from the selected nickel (II) salt, the solution containing Ni (II) ions;
   precipitating Ni (II) ions as nickel hydroxide from the glycol solution by the addition of an aqueous solution of a carbonate salt to the solution of nickel (II) acetate in ethylene glycol;
   separating the nickel hydroxide precipitate from the mother liquor to recover α-Ni(OH)$_2$; and
   calcining the α-Ni(OH)$_2$ in air at a temperature in the range of about 573K to about 1073K to form nanometer-size diameter fiber particles of nickel oxide.

10. A method of forming nanometer-size particles as recited in claim 9, the method further comprising:
    reducing the particles of nickel oxide with hydrogen to from nanometer-size particles of nickel.

* * * * *